United States Patent [19]

Hofmann et al.

[11] 4,010,124

[45] Mar. 1, 1977

[54] PROCESS FOR FLAMEPROOFING POLYURETHANES

[75] Inventors: Peter Hofmann; Peter Rohringer, both of Basel, Switzerland

[73] Assignee: Ciba-Geigy Corporation, Ardsley, N.Y.

[22] Filed: Apr. 2, 1975

[21] Appl. No.: 564,410

Related U.S. Application Data

[63] Continuation-in-part of Ser. No. 399,577, Sept. 21, 1973, abandoned, which is a continuation of Ser. No. 266,194, June 26, 1972, abandoned.

[30] Foreign Application Priority Data

July 5, 1971 Switzerland .................... 9829/71

[52] U.S. Cl. ..................... 260/2.5 AJ; 260/45.7 P
[51] Int. Cl.² ........................................ C08K 5/53
[58] Field of Search ............... 260/28.5 R, 45.7 P, 260/928, 30.6 R, 2.5 AJ; 106/15 FP

[56] References Cited

UNITED STATES PATENTS 3,737,397  6/1973  Baranauckas ................. 260/2.5 AJ

FOREIGN PATENTS OR APPLICATIONS 1,316,948  5/1973  United Kingdom

*Primary Examiner*—Paul R. Michl
*Attorney, Agent, or Firm*—Luther A. R. Hall

[57] ABSTRACT

A process for flameproofing polyurethanes, particularly polyurethane foams, is provided. It consists in adding a reaction product from dimethyl methanephosphonate, an aliphatic diol or triol and a lower epoxide to the polyurethane components. These reaction products are non-uniform mixtures of different esters of methane phosphonic acid.

7 Claims, No Drawings

PROCESS FOR FLAMEPROOFING POLYURETHANES

RELATED APPLICATIONS

This application is a continuation in part of copending application Ser. No. 399,577, filed on Sept. 21, 1973 now abandoned, which is a continuation of application Ser. No. 266,194, filed on June 26, 1972 now abandoned.

The subject of the invention is a process for flameproofing plastics, characterised in that a reaction product of
1. a phosphonic acid ester of the formula

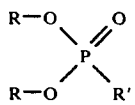

wherein R and R' each denote alkyl with 1 to 4 carbon atoms,
2. an alcohol of the formula $$X-OH \qquad (2)$$

wherein X denotes alkyl with 3 to 22 carbon atoms, hydroxyalkyl with 2 to 6 carbon atoms or halogenoalkyl with 2 to 5 carbon atoms, with the boiling point of the alcohol of the formula $$R-OH$$

wherein R has the indicated meaning, which is liberated during the reaction, being at least 30° C below the boiling point of the alcohol X—OH, and
3. optionally, an epoxide with 2 to 4 carbon atoms, is incorporated into the plastics.

The radicals R and R' in the formulae (1) and (3) are different from one another, or, preferably, identical with one another. These alkyl radicals are, for example, n-butyl, isopropyl, n-propyl, ethyl or, preferably, methyl.

Preferably, methanephosphonic acid dimethyl ester is used as component (1) in the process according to the invention.

The radical X in the formula (2) is derived from monohydric or polyhydric alkanols, for example from stearyl alcohol, lauryl alcohol, n-octanol, n-hexanol, n-, 1- or 2-butanol; polyols, such as glycerine or, preferably, diols such as ethylene glycol, 1,2-n-propanediol, 1,4-n-butanediol or 1,5-n-pentanediol; or halogenoalkanols, for example 1;2-dibromopropanol, chlorohydrin or trichloroethanol; halogen here as a rule denotes iodine or especially bromine or chlorine.

Where the alcohol of the formula (2) is a polyol, reaction products which contain more than one radical, for example 2 to 6, preferably 2, radicals of the formula (2), can be obtained.

Preferably, an alcohol of the formula $$X_1-OH \qquad (4)$$

wherein $X_1$ denotes alkyl with 3 to 22, preferably 3 to 5, carbon atoms or hydroxyalkyl with 2 to 6 carbon atoms, is used for the manufacture of the products employed according to the invention.

Further alcohols which are suitable are above all those of the formula $$X_2-OH \qquad (5)$$

wherein $X_2$ denotes hydroxyalkyl, preferably monohydroxyalkyl or dihydroxyalkyl, with 2 to 6 carbon atoms, and especially ethylene glycol and 1,2-propanediol. In addition, glycerine is of outstanding interest.

The manufacture of the esterification products is carried out in the presence of alkali metal oxides or preferably alkaline earth metal oxides or alkaline earth metal hydroxides. As such it is possible to use, for example, $Na_2O$, $K_2O$, SrO, BaO, $Mg(OH)_2$ or $Ca(OH)_2$ or above all MgO and especially CaO. The oxides can also be employed as mixtures, optionally also mixed with other metal oxides such as, for example, lead-II oxide. Where the components (1) are pure products, free of dimethyl phosphite or trimethyl phosphite, the reaction products can also be manufactured in the presence of acid catalysts such as p-toluenesulphonic acid, $MgCl_2$, $ZnCl_2$, $H_2SO_4$, HCl, $H_3PO_4$ or $PCl_3$.

The trans-esterification is appropriately carried out at temperatures of 95° to 220° C, preferably 150° – 200° C or especially 160° to 185° C.

The molar ratio of the starting components can vary within wide limits but is generally, depending on the functionality of the alcohol, 6:1 to 1:3, preferably 2:1 to 1:3 (phosphonic acid ester : alcohol). The trans-esterification is particularly advantageously carried out with 1 – 2 mols of phosphonic acid ester and 1 mol of alcohol and 0 to 1 mol of epoxide.

The optionally conjointly used component (3) is, for example, 1,2-butylene oxide or preferably ethylene oxide or especially 1,2-propylene oxide.

The reaction products used according to the invention are complex mixtures of products of differing composition. In addition to smaller proportions of starting product, these mixtures containing products which probably, for example in the case where methanphosphonic acid dimethyl ester, glycerine and 1,2-propylene oxide are used as the starting products, for example correspond to the following formulae:

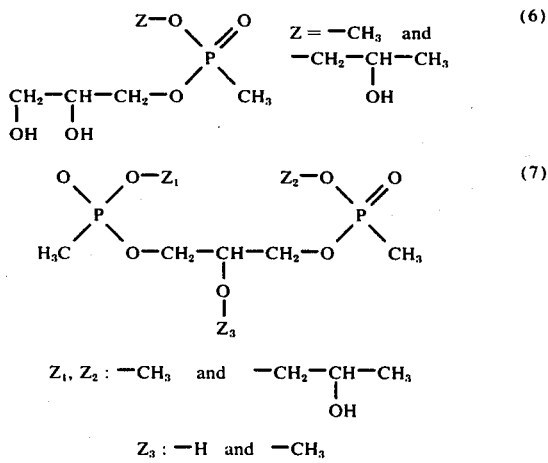

Analogous mixtures are obtained on using other starting products.

Suitable plastics for flameproofing are, for example, viscose, with the reaction being added to the spinning composition, or above all polyurethanes, preferably polyurethane foams or coatings. In particular, polyurethane foams are suitable for being rendered of low inflammability according to the process of the invention.

The reaction products are appropriately incorporated into the polyurethane foams or coatings by adding them to the mixture for the manufacture of the foams, or adding them to the coating compositions.

These manufacturing mixtures have the composition which is customary for the manufacture of polyurethane foams. They contain, as a rule, polyesters or polyethers having free hydroxyl groups and a molecular weight of 400 to 6,000, for example polyols and diisocyanates, such as, for example, 4,4'-diphenylmethane-diisocyanate or toluylenediisocyanate, as the reactants. As blowing agents required for foam formation, the mixtures contain, for example, fluorotrichloromethane or difluorodichloromethane. As an activating additive the mixtures can furthermore contain a tertiary amine, such as, for example, diaminobicyclooctane. As further activating additives, the mixtures can contain metal salts, such as, for example, tin octoate.

Appropriately, 1 to 15%, preferably 5 to 10%, of the flameproofing component containing phosphorus are used relative to the solids content of the reaction mixtures for the manufacture of polyurethane foam.

The phosphorus compounds incorporated into the polyurethane foams give extremely flameproof foams. Furthermore, additions of such phosphorus compounds hardly interfere with the manufacturing process of the foams.

In part, the present phosphorus compounds admittedly have an activating or retarding effect on the course of the reaction of polyurethane formation, but this influence can be controlled by appropriate choice of the amount of blowing agents and activators added. The mechanical properties are also not influenced significantly by the addition of the phosphorus compounds, in that practically no distortion occurs.

This process can be used for flameproofing so-called rigid and soft polyurethane foams. The process is also used for flameproofing polyurethane coatings on fibrous substrates.

Polyesters and especially also polyethers, such as are used in the process according to the invention for the manufacture of the polyurethanes, are described in detail, for example in "Kunststoff-Handbuch (Plastics Handbook), volume VI, Polyurethanes, Carl Hanser Verlag Munich 1966".

It is particularly advantageous to employ halogen-free reaction products in the process according to the invention, since they do not evolve any hydrogen halide gases on combustion.

In the manufacturing instructions and examples which follow, percentages are percentages by weight.

Manufacturing Instructions

A. 77 g (1 mol) of 1,2-n-propanediol and 124 g (1 mol) of methanephosphonic acid dimethyl ester are treated with 3.7 g (0.05 mol) of calcium hydroxide. Thereafter, 32 g (1 mol) of methanol are distilled off over the course of 1 hour at 175° C. The residue obtained consists of 169 g of a product which probably contains substantial proportions of products of the formula

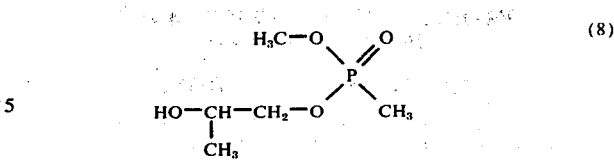

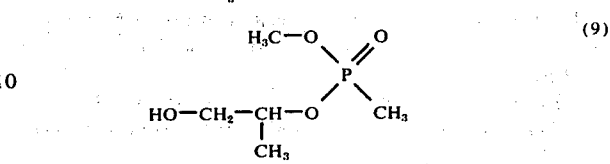

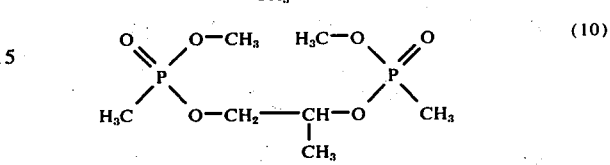

and

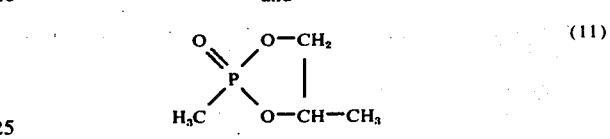

B. 920 g (10 mols) of glycerine and 2,480 g (20 mols) of 99% strength methanephosphonic acid dimethyl ester are treated with 56 g (1 mol) of calcium oxide. Thereafter 504 g of distillate of boiling point 45° – 65° C are distilled off over the course of 4 – 5 hours at a bath temperature of 160° – 170° C and an internal temperature of 155° 14 160° C in the flask. The analysis of the distillate shows 90.7%, corresponding to 14.3 mol of methanol.

In the residue, 0.43 mol of H$^+$ per mol of phosphorus are found by acidimetric titration.

574 g (10 mols) of propylene oxide are added dropwise to the 2.952 g of residue and the whole is heated under reflux at 80° C for 4 hours. Thereafter, 49 g of unreacted propylene oxide are distilled off, amounting to a consumption of 525 g (9 mols) of propylene oxide.

The acidimetric titration shows 0.07 mol of H$^+$ per mol of phosphorus.

Viscosity: 506 cSt.

C. 92 g (1 mol) of glycerine (anhydrous) and 248 g (2 mols) of 99% strength methanephosphonic acid dimethyl ester are treated with 5.6 g (0.1 mol) of calcium oxide. Thereafter, 25 g of distillate of boiling point 30° – 66° C are distilled off over the course of 4 – 5 hours at a bath temperature of 170° – 175° C and an internal temperature of 155° – 160° C in the flask. The analysis of the distillate shows 98.9%, corresponding to 0.77 mol of methanol.

0.37 mol of H$^+$ per mol of phosphorus are determined in the residue by acidimetric titration.

The total residue from the trans-esterification is esterified with 52.5 g (0.91 mol) of propylene oxide at 70° – 76° C for 6 hours. The acid content of the product is 0.05 mol of H$^+$ per mol of phosphorus and the phosphorus content is 19.1%.

Viscosity: 782 cSt.

D. 950 g (10 mols) of glycerine are rendered anhydrous by azeotropic distillation with 200 g of xylene. Thereafter, 2,480 g (20 mols) of dimethylmethane-phosphonate (96% strength) and 56 g (1 mol) of calcium oxide are added. The trans-esterification takes place at 170° C for 4 hours, in the course of which 1,014 g of distillate distil off.

The resulting product contains 0.32 mol of H$^+$ per mol of phosphorus.

518 g of propylene oxide are added dropwise to 1,307 g of the residue and the mixture is heated under reflux at 80° C for 4 hours. The resulting product contains 0.02 mol of H$^+$ per mol of phosphorus.

Viscosity: 25,000 cSt.

800 g of trans-esterified product are heated to 90° C and alkalene oxide is then injected. In the course thereof, the temperature rises to 105° C; after 4 hours, the reaction is complete and 123 g of ethylene oxide have been absorbed. The resulting product contains 0.005 mol of H$^+$ per mol of phosphorus.

Viscosity: 13,000 cSt.

E. 166 g (1 mol) of diethylethanephosphonate and 46 g (0.5 mol) of glycerine together with 8.6 g (0.05 mol) of p-toluenesulphonic acid are trans-esterified for 3 hours at a bath temperature of 185° C and an internal temperature of 175° C in the flask. The amount of distillate is 27 g and the acid content in the residue is 0.905 mol of H$^+$ per mol of phosphorus.

The residue is esterified with 100 g of propylene oxide at 80° C for 4 hours.

The viscosity of the product is 51 cSt.

F. 256 g (1 mol) of stearyl alcohol and 257 g (2 mols) of methanephosphonic acid dimethyl ester (96% strength) are treated with 5.6 g (0.1 mol) of calcium oxide. Thereafter, 27.5 g of distillate of boiling point 62° – 81° C are distilled off over the course of 3 hours at a bath temperature of 185° C and an internal temperature of 170° – 175° C in the flask.

0.4 mol of H$^+$ per mol of phosphorus are determined in the residue by acidimetric titration.

The residue is esterified with 36.6 g (0.63 mol) of propylene oxide. The amount of the resulting product is 547 g and the acid content is 0.004 mol of H$^+$ per mol of phosphorus.

G. 465 g (7.5 mols) of distilled, anhydrous ethylene glycol and 2580 g (20 mols) of methanephosphonic acid dimethyl ester (96.3%) are treated with 56 g (1 mol) of calcium oxide. Thereafter at a bath temperature of 160° C, 470 g of a product having a boiling range of 60° to 90° C under normal pressure and 1174 g of a product having a boiling range of 100° to 120° C at 14 mm Hg are distilled off. The residue is homogeneous and very acid, it contains 1.4. 10$^{-3}$ mol of H$^+$ per g.

1092 g of the residue then are reacted with 180 g of propylene oxide at 75° C. This product contains only 2.4. 10$^{-5}$ mol of H$^+$ per g.

EXAMPLE 1

A mixture of 20 g of a polyol which reacts slowly (a polyether of molecular weight about 1,000, from trimethylolpropane), 8 g of fluorotrichloromethane, 21.8 g of 4,4'-diphenylmethanediisocyanate, 0.2 g of an activator based on an amine and 5 g of the product according to Instruction A is stirred for one minute with a simple paddle stirrer at 1,000 revolutions per minute. Thereafter the mass which is foaming up is immediately introduced into a tube of 5.5 cm diameter and the reaction is allowed to go to completion in the tube, this requiring 10 hours. A foam without addition of product according to Example 1 is manufactured simultaneously.

Test of Flameproof Character

One specimen at a time, of size 120 mm × 30 mm × 10 mm, is fixed with the 120 mm edge at an angle of 45° to the horizontal and the 30 mm edge horizontal.

Marks are made at 25 mm and 100 mm. The samples are ignited at the lower end for 5 seconds by means of a fishtail burner. The following values are found:

|  | Sample without additive 1 | Sample with additive 2 |
|---|---|---|
| Duration of burning, seconds | 15 | 2 |
| 25 mm mark | reached | not reached |
| 100 mm mark | reached | not reached |
| Loss in weight | 80% | 21% |

EXAMPLE 2

A soft foam is manufactured by mixing the following materials: 100 g of a polyhydroxy compound of a polyether, of molecular weight about 3,000 (manufactured from trimethylolpropane), suitable for the formation of a soft polyurethane foam, 1 g of siloxane-oxyalkylene copolymer, 0.32 g of tin-II octoate, 3.5 g of water, 48.2 g of toluylene-diisocyanate (80 : 20 mixture of 2,4/2,6 isomer) and 10 g of flameproofing agent.

ASTM D 1692 - Test Method

One test specimen at a time, of size 150 mm × 50 mm × 13 mm, is fixed with the 50 mm × 13 mm edge horizontal. Marks are made at 25 mm and 100 mm. The sample is then ignited at the lower end by means of a fishtail burner.

The ignition time is 60 seconds. If the burnt zone is not longer than 25 mm, the foam is described as noninflammable.

If the sample burns beyond the 25 mm mark and the burnt zone is smaller than 125 mm, the foam is described as self-extinguishing. The length of the burnt zone is quoted in centimeters.

If the sample burns beyond the 125 mm mark, the foam is described as inflammable and the speed of burning is quoted.

TABLE

|  | Without additive | Product according to Instruction | | | | | |
|---|---|---|---|---|---|---|---|
|  |  | B | C | D | E | F | G |
| Elementary analysis: % of phosphorus |  | 19.1 | 19.1 | 19 | 19 | 14.4 | 11.4 |
| Hydroxyl number: |  | 252 | 250 | 256 | 260 | 255 | 79 |
| Flameproofing action: |  |  |  |  |  |  |  |
| 1. Sheets: of polyurethane, glassfiber-reinforced, approx. 220 g/m² |  |  |  |  |  |  |  |
| Limiting oxygen index. |  |  |  |  |  |  |  |
| Difference between absence of additive and presence of 30% of product, × 10$^{-3}$ |  | 57 | 53 | 55 | 60 | 36 | 26 |
| 2. Soft foam |  |  |  |  |  |  |  |

TABLE-continued

| | Without additive | Product according to Instruction | | | | | |
|---|---|---|---|---|---|---|---|
| | | B | C | D | E | F | G |
| Amount used, in % of polyol | | 10 | 10 | 10 | 10 | 10 | 10 |
| a) Foaming behaviour | | | | | | | |
| Cream time in seconds | 10 | 10 | 12 | 12 | 12 | 7 | 8 |
| Rising time in seconds | 90 | 100 | 110 | 130 | 130 | 100 | 130 |
| Crosslinking time in minutes | 10 | 3 | 3 | 3 | 2 | 3 | 5 |
| b) Burning behaviour (ASTM D 1692) | | | | | | | |
| Burnt zone in cm | 15 | 4 | 5 | 6.5 | 6.5 | 3.5 | 7.5 |
| Speed of burning | 1.8 mm/sec | | | | | | |

The OH number (hydroxyl number) is the amount of KOH, in mg, which corresponds to the amount of acetic anhydride which is required for the esterification of 1 g of the flameproofing component.

Individual samples are furthermore subjected to the flameproofing test after ageing at 140° C (dry) for 1, 2 and 4 days.

| | B | C | D | E | F |
|---|---|---|---|---|---|
| After 1 day | 5 cm | 5 cm | 10 cm | 5 cm | 5.5 cm |
| 2 days | 4 cm | 6 cm | 4.5 cm | 4.5 cm | 6 cm |
| 4 days | 9 cm | 4.5 cm | 4 cm | 8 cm | 4.5 cm |

Additionally, the flameproof character was tested after 7 days ageing in the case of two samples:
B: 4 cm
C: 6.5 cm.

EXAMPLE 3

In the same manner as indicated in Example 2 a polyurethane foam is manufactured and tested according the ASTM D-1692 test method:

| Amount of flameproofing agent G in % of the polyol | 10 | |
|---|---|---|
| Cream time | 10 | seconds |
| Rising time | 12 | seconds |
| Crosslinking time | 3 | minutes |
| Burnt zone after | | |
| 1 day at 140° C. | 5 | cm |
| 2 days at 140° C. | 5 | cm |
| 4 days at 140° C. | 5 | cm |

EXAMPLE 4 a. Polyester-polyol

A polyester-polyol is prepared according to example 30 of U.S. patent 3,737,397 from 670 g (5 moles) of trimethylolpropane and 438 g (3 moles) of adipic acid in 1 l of xylene in the presence of 1 g of an strongly acidic ion exchanges by 14 hours of boiling with azeotropic separation of the formed water. After filtering off the ion exchanger the xylene is distilled off under reduced pressure. There is obtained 956 g of a polyester-polyol which has an acid number of 30 and a hydroxyl number of 492.

b. Prepolymer

A prepolymer is prepared according to example 30 of U.S. pat. No. 3,737,397 from 20 parts of the mentioned polyester-polyol and 80 parts of a commercial toluene diisocyanate ("Desmodur T 80", Bayer A.G.) consisting of 80% 2,4- and 20% 2,6-toluene diisocyanate. The mixture is stirred 20 minutes at room temperature and 2 hours at 90° C.

c. Foam preparation

The polyester-polyol (a) and a phosphonate according to the Manufacture Instruction G (OH number 364) are mixed in different weight ratios as it is listed in the recipes of table 1. There is added to each mixture 0.5 g of "Silicon Surfactant L 520" (Dow Corning Comp.), 0.8 g of dimethyl aminoethanol and 28 g of trichlorofluoromethane. To this mixtures are added the indicated amounts of the prepolymer (b) under violent stirring. After one minute the mixture is poured into a cylindrical form. The resulting foam is tested for its flamability by measuring the Oxygen Index according to ASTM method 2863 and the burning velocity according to ASTM method D 1692. For comparison in recipe 4 a foam is made without the addition of any phosphonate and in recipes 5 and 6 foams are made using a phosphonate which has been prepared according to example 29 of U.S. pat. No. 3,737,397 from triphenyl phosphite, trimethylol propane and epichlorohydrine. The results are shown in table 1.

Table 1

| Recipes | 1 | 2 | 3 | 4 | 5 | 6 | |
|---|---|---|---|---|---|---|---|
| Polyester-polyol (a) | 70 | 80 | 90 | 100 | 70 | 70 | g |
| Phosphonate G | 30 | 20 | 10 | — | — | — | g |
| Phosphonate according to USP 3,737,397 | — | — | — | — | 30 | 30 | g |
| Trichloro fluoromethane | 28 | 28 | 28 | 28 | 28 | 8 | g |
| Silicon Surfactant | 0.5 | 0.5 | 0.5 | 0.5 | 0.5 | 0.5 | g |
| Dimethylaminoethanol | 0.8 | 0.8 | 0.8 | 0.8 | 0.8 | 0.8 | g |
| Prepolymer (b) | 113 | 116 | 116 | 121 | 129 | 129 | g |
| Foam, density | 37.8 | 36.3 | 36.0 | 38.0 | 29.3 | 39.7 | g/l |
| compressions yield | 22.8 | 35.8 | 46.7 | 18.1 | — | — | |
| Flamability | | | | | | | |
| Oxygen Index (ASTM 2863) | 0.242 | 0.220 | 0.204 | 0.165 | 0.193 | 0.193 | |
| | 0.077 | 0.055 | 0.039 | 0.00 | 0.028 | 0.028 | |
| burning velocity (ASTM D 1692) | 3.5 | 3.0 | 6.1 | 13.8 | 8.7 | 7.6 | cm/min |
| Burned length | 3.0 | 4.5 | 12.5 | 12.5 | 12.5 | 12.5 | cm |

From these results it is obvious that the addition of 10 parts phosphonate G causes a higher flame protection than the addition of 30 parts of a phosphonate according to U.S. Pat. No. 3,737,397.

We claim:

1. An improved process for flameproofing polyurethanes using 1 to 15 percent by weight based on the polyurethane of a reactive phosphonate as flameproofing agent wherein the improvement comprises
    incorporating as the flameproofing agent the reaction product based on a molar ratio of (1) 1 to 2 mols of dimethyl methanephosphonate; (2) 0.75 to 1 mol of an alkanediol or alkanetriol of 2 to 6 carbon atoms; and (3) 0 to 1 mol of an epoxide having 2 to 4 carbon atoms; into a mixture of polyol and diisocyanate components from which the polyurethane is produced.

2. A process according to claim 1, wherein the reaction component (2) is ethylene glycol, 1,2-propanediol or glycerol.

3. A process according to claim 1, wherein the reaction component (3) is propylene oxide or ethylene oxide.

4. A process according to claim 1, wherein a reaction product from dimethyl methanephosphonate, ethylene glycol and propylene oxide is used as flameproofing agent.

5. A process according to claim 1, wherein a flameproofing agent is used which is obtained by reacting the components (1), (2) and (3) at 95° to 220° C in the presence of an alkali metal oxide, alkaline earth metal oxide or alkaline earth metal hydroxide.

6. A polyurethane flameproofed according to the process of claim 1.

7. A polyurethane according to claim 6 in form of a foam.

* * * * *